United States Patent [19]

Dürr et al.

[11] 4,079,144
[45] Mar. 14, 1978

[54] PHENYLIMINO-THIAZOLINES AND THEIR USE AS ACARICIDES

[75] Inventors: Dieter Dürr, Bottmingen; Walter Traber, Reinach, both of Switzerland

[73] Assignee: Ciba-Geigy Corporation, Ardsley, N.Y.

[21] Appl. No.: 681,308

[22] Filed: Apr. 29, 1976

[30] Foreign Application Priority Data

May 7, 1975 Switzerland ............... 5894/75

[51] Int. Cl.$^2$ ............... C07D 277/18; A01N 9/12
[52] U.S. Cl. ............... 424/270; 260/306.7 T; 260/552 A
[58] Field of Search ............... 260/306.7 T; 424/270

[56] References Cited
PUBLICATIONS
Ciba Ltd., Chem. Abstracts, 60:P12019d (1963).

Primary Examiner—Richard J. Gallagher
Attorney, Agent, or Firm—Harry Falber

[57] ABSTRACT

Novel acaricidally effective thiazoline compounds corresponding to the general formula

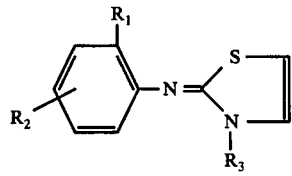

wherein $R_1$ and $R_2$, independently of one another, represent chlorine, methyl or ethyl, whereby $R_2$ can occupy the 4- or 6-position, with the exception that if $R_1$ and $R_2$ represent chlorine, $R_2$ cannot be in the 4-position, $R_3$ represents a straight-chain or branched-chain alkyl group having 1 to 4 carbon atoms, optionally substituted by alkoxy having 1-2 carbon atoms, or a straight-chain or branched-chain alkenyl group having 3 to 5 carbon atoms, optionally substituted by halogen including the acid addition salts, particularly the hydrochlorides, and compositions containing these compounds, as well as the use of these compounds for combatting mites, particularly ticks.

9 Claims, No Drawings

PHENYLIMINO-THIAZOLINES AND THEIR USE AS ACARICIDES

The present invention relates to novel acaricidally effective thiazoline compounds, to the production of these compounds, to compositions containing these compounds, as well as to the use of these compounds for combatting mites, particularly ticks.

The novel compounds correspond to the general formula

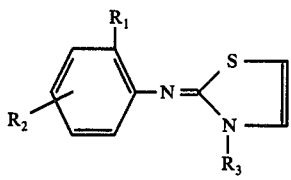

wherein $R_1$ and $R_2$, independently of one another, represent chlorine, methyl or ethyl, whereby $R_2$ can occupy the 4- or 6-position, with the exception that if $R_1$ and $R_2$ represent chlorine, $R_2$ cannot be in the 4-position, $R_3$ represents a straight-chain or branched-chain alkyl group having 1 to 4 carbon atoms, optionally substituted by alkoxy having 1-2 carbon atoms, or a straight-chain or branched-chain alkenyl group having 3 to 5 carbon atoms, optionally substituted by halogen, and include the acid addition salts, particularly the hydrochlorides.

By alkyl groups according to formula I are meant the methyl, ethyl, n-propyl, isopropyl, n-butyl, sec.butyl or tert.butyl group; and by alkenyl groups according to formula I which are optionally substituted by halogen atoms are meant the allyl, crotonyl, methallyl, 2,2-dimethylvinyl, 2-chloroallyl, 3-chloroallyl or 2,3-dichloroallyl group.

Suitable salts of compounds of the formula I are, in addition to the hydrochlorides: sulphates, phosphates, perchlorates, acetates, lactates, succinates, citrates or naphthalenedisulphonates.

Biologically active thiazoline compounds are already known. Thus the compounds of the formula I belong to a group of thiazolines which are disclosed as pest-control agents in the Swiss Pat. No. 439,858. In the said patent specification, however, the compounds of the formula I according to the invention are not described with respect to their mode of acting or in any way explicitly mentioned.

It has now been shown that, surprisingly, the compounds of the formula I according to the invention have an excellent action against acarids, especially with regard to the inhibition of the oviposition of ticks, and in this respect are far superior to the hitherto known compounds which act in this way.

The following compounds are characterised by particularly high degrees of activity:
2-(2-methyl-4-chlorophenylimino)-3-methyl-thiazoline and
2-(2,4-dimethyl-phenylimino)-3-methyl-thiazoline.

There are available for the production of thiazolines known methods of synthesis by which thioureas are reacted with α-halogenocarbonyl compounds in the presence of polar solvents at elevated temperature.

The compounds of the formula I can thus be produced in a manner known per se by reacting a compound of the formula

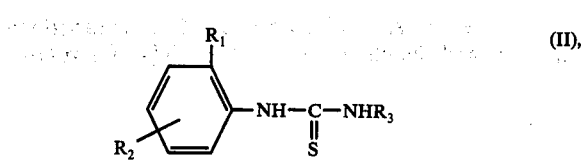

wherein the radicals $R_1$ to $R_3$ have the meanings given under formula I, with chloroacetaldehyde in a polar solvent such as water or alcohol at elevated temperature, and using in the event of the chloroacetaldehyde being present in the form of diethylacetal dilute mineral acid as the reaction medium.

The thioureas of the formula II used as starting compounds are known and can be produced by methods already described. They can be obtained, for example, by reaction either of phenylisothiocyanates with amines, or of phenylamines with isothiocyanates according to the following pattern of synthesis:

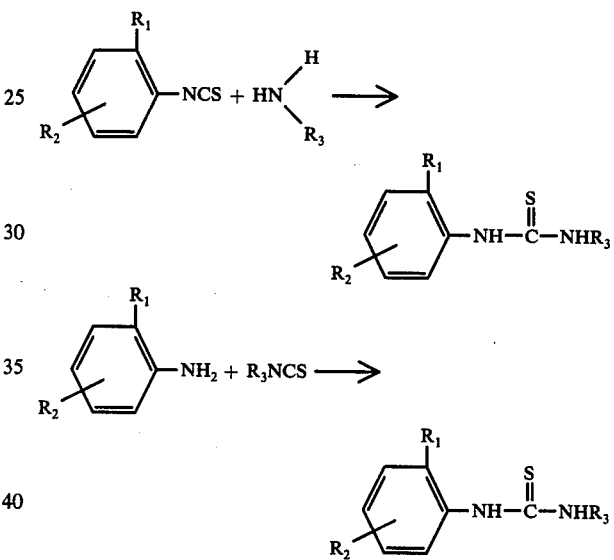

EXAMPLE 1

2-(2,4-xylylimino)-3-methyl-thiazoline 19.4 g (0.1 mole) of N-2,4-xylyl-N'-methyl-thiourea and 15.2 g (0.1 mole) of chloroacetaldehyde-diethylacetal in 150 ml of 2N aqueous hydrochloric acid are refluxed for 1 hour. The clear light-yellow solution is subsequently cooled to room temperature; it is rendered slightly alkaline with 30% aqueous medium hydroxide solution, and extracted with ether. The ether extract is washed with water, dried with sodium sulphate and filtered, and the ether is then distilled off. The oily residue is distilled; b.p. 132°–134° C/0.3 Torr; yield: 20.2 g = 92% of theory.

EXAMPLE 2

2-(2,6-dichlorophenyl)-3-methyl-thiazoline 28 g (0.12 mole) of N-(2,4-dichlorophenyl)-N'-methyl-thiourea and 32 g (0.12 mole) of 30% aqueous chloroacetaldehyde solution are refluxed, with mechanical stirring, in 100 ml of water for 3 hours. The clear solution is cooled to room temperature, and rendered slightly alkaline with 30% aqueous sodium hydroxide solution. Extraction is then performed with ether; the ether phase is washed with water and dried with sodium sulphate, and the ether is distilled off. The oily residue is distilled in a bulb tube; b.p. 140° C/0.005 Torr: 21.7 g of white crystals, m.p. 88°–90° C (70% of theory).

The following thiazolines of the formula I are obtained in an analogous manner:

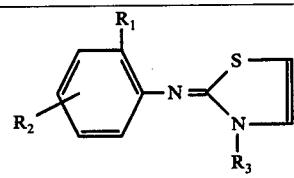
(I)

| Comp. No. | $R_1$ | $R_2$ | $R_3$ | Physical data |
|---|---|---|---|---|
| 1 | Cl | 6-Cl | $CH_3$ | 88–90° C 140° C/0,005 Torr |
| 2 | Cl | 6-$CH_3$ | $CH_3$ | 86–88° C |
| 3 | $CH_3$ | 6-$CH_3$ | $CH_3$ | 83–85° C |
| 4 | $C_2H_5$ | 6-$C_2H_5$ | $CH_3$ | 58–59° C |
| 5 | $CH_3$ | 4-Cl | $CH_3$ | 66° C |
| 6 | $CH_3$ | 4-$CH_3$ | $CH_3$ | 132–134° C/0,3 Torr |
| 7 | $CH_3$ | 4-$CH_3$ | $C_4H_9$ | 156–15° C/0,4 Torr $n_D^{20}$ 1,5919 |
| 8 | $CH_3$ | 4-$CH_3$ | $(CH_3)_2CH$ | 49–51° C |
| 9 | $CH_3$ | 4-$CH_3$ | $(CH_3)_3$—C | 53° C |
| 10 | $CH_3$ | 4-$CH_3$ | $CH_2=CH-CH_2$ | $n_D^{20}$ 1,6149 |
| 11 | $CH_3$ | 4-$CH_3$ | $C_3H_7$ | $n_D^{20}$ 1,6023 |
| 12 | $CH_3$ | 4-$CH_3$ | $CH_3-CH=CH-CH_2$ | |
| 13 | $CH_3$ | 4-$CH_3$ | $(CH_3)_2CH-CH_2$ | $n_D^{20}$ 1,5913 |
| 14 | $CH_3$ | 4-$CH_3$ | $C_2H_5$ | 65° C |
| 15 | Cl | 4-$CH_3$ | $CH_3$ | 92–94° C |
| 16 | $CH_3$ | 6-$C_2H_5$ | $CH_3$ | 160° C/0,3 Torr |
| 17 | $CH_3$ | 4-Cl | $CH_3$ | 85–88° C |
| 18 | $CH_3$ | 4-$CH_3$ | $CH_2=\underset{\underset{CH_3}{\mid}}{C}-CH_3$ | 120–127/0,001 Torr |
| 19 | $CH_3$ | 4-$CH_3$ | $CH_2=CCl-CH_2$ | |
| 20 | $CH_3$ | 4-$CH_3$ | $ClCH=CH-CH_2$ | |
| 21 | $CH_3$ | 4-$CH_3$ | $ClCH=CCl=CH_2$ | |
| 22 | Cl | 6-Cl | $C_2H_5$ | 149–152°/0,001 Torr |
| 23 | $CH_3$ | 4-Cl | $-\underset{\underset{CH_3}{\diagup}}{CH}-CH_2-OCH_3$ | 138–140°/0,03 |
| 24 | Cl | 6-Cl | $C_3H_7$ | 150°/0,001 Torr |
| 25 | Cl | 6-Cl | $C_4H_9$ | 140°/0,001 Torr |
| 26 | Cl | 6-Cl | $(CH_3)_2CH$ | 130–135°/0,001 Torr |
| 27 | Cl | 6-Cl | $(CH_3)_3C$ | |
| 28 | Cl | 6-Cl | $CH_2=CH-CH_2$ | 150–155°/0,001 Torr |
| 29 | Cl | 6-Cl | $(CH_3)_2CH-CH_2$ | 147–152°/0,001 Torr |
| 30 | Cl | 6-Cl | $CH_2=CCl-CH_2$ | |
| 31 | Cl | 6-Cl | $ClCH=CH-CH_2$ | |
| 32 | Cl | 6-Cl | $ClCH=CCl-CH_2$ | |
| 33 | Cl | 6-Cl | $CH_3-CH=CH-CH_2$ | |
| 34 | Cl | 6-Cl | $CH_2=\underset{\underset{CH_3}{\mid}}{C}-CH_2$ | |
| 35 | $CH_3$ | 6-$C_2H_5$ | $C_2H_5$ | 130°/0,03 Torr |
| 36 | $CH_3$ | 6-$C_2H_5$ | $C_3H_7$ | 119°/0,001 Torr |
| 37 | $CH_3$ | 6-$C_2H_5$ | $C_4H_9$ | 129–135°/0,001 Torr |
| 38 | $CH_3$ | 6-$C_2H_5$ | $(CH_3)_2CH$ | 130°/0,01 Torr |
| 39 | $CH_3$ | 6-$C_2H_5$ | $(CH_3)_3C$ | 134°/0,005 Torr |
| 40 | $CH_3$ | 6-$C_2H_5$ | $CH_2=CH-CH_2$ | 140°/0,01 Torr |
| 41 | $CH_3$ | 6-$C_2H_5$ | $(CH_3)_2-CH-CH_2$ | 128°/0,005 Torr |
| 42 | $CH_3$ | 6-$C_2H_5$ | $CH_2=CCl-CH_2$ | |
| 43 | $CH_3$ | 6-$C_2H_5$ | $ClCH=CH-CH_2$ | |
| 44 | $CH_3$ | 6-$C_2H_5$ | $ClCH=CCl-CH_2$ | |
| 45 | $CH_3$ | 6-$C_2H_5$ | $CH_3-CH=CH-CH_2$ | |
| 46 | $CH_3$ | 6-$C_2H_5$ | $CH_2=\underset{\underset{CH_3}{\mid}}{C}-CH_2$ | 120–127°/0,001 Torr |
| 47 | Cl | 4-$CH_3$ | $C_2H_5$ | 145–150°/0,0025 Torr |
| 48 | Cl | 4-$CH_3$ | $C_3H_7$ | 150°/0,005 Torr |
| 49 | Cl | 4-$CH_3$ | $C_4H_9$ | 155°/0,005 Torr |
| 50 | Cl | 4-$CH_3$ | $(CH_3)_2CH$ | 135°/0,005 Torr |
| 51 | Cl | 4-$CH_3$ | $(CH_3)_3C$ | 155–160°/0,0001 Torr |
| 52 | Cl | 4-$CH_3$ | $CH_2=CH-CH_2$ | 165°/0,0001 Torr |
| 53 | Cl | 4-$CH_3$ | $(CH_3)_2-CH-CH_2$ | |
| 54 | Cl | 4-$CH_3$ | $CH_2=CCl-CH_2$ | |
| 55 | Cl | 4-$CH_3$ | $ClCH=CH-CH_2$ | |
| 56 | Cl | 4-$CH_3$ | $CH_3-CH=CH-CH_2$ | |
| 57 | Cl | 4-$CH_3$ | $CH_2=\underset{\underset{CH_3}{\mid}}{C}-CH_2$ | |
| 58 | $CH_3$ | 4-Cl | $C_2H_5$ | 148°/0,01 Torr |
| 59 | $CH_3$ | 4-Cl | $C_3H_7$ | 122–130°/0,008 Torr |
| 60 | $CH_3$ | 4-Cl | $C_4H_9$ | 145°/0,005 Torr |
| 61 | $CH_3$ | 4-Cl | $(CH_3)_2CH$ | 139–145°/0,01 Torr |
| 62 | $CH_3$ | 4-Cl | $(CH_3)_3C$ | 135–140°/0,007 Torr |

-continued

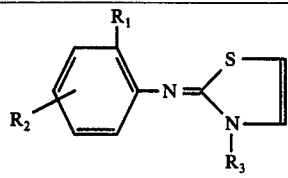
(I)

| Comp. No. | $R_1$ | $R_2$ | $R_3$ | Physical data |
|---|---|---|---|---|
| 63 | CH₃ | 4-Cl | CH₂=CH—CH₂ | 135–140°/0,01 Torr |
| 64 | CH₃ | 4-Cl | (CH₃)₂—CH—CH₂ | 147°/0,01 Torr |
| 65 | CH₃ | 4-Cl | CH₂=CCl—CH₂ | |
| 66 | CH₃ | 4-Cl | ClCH=CH—CH₂ | |
| 67 | CH₃ | 4-Cl | ClCH=CCl—CH₂ | |
| 68 | CH₃ | 4-Cl | CH₃—CH=CH—CH₂ | |
| 69 | CH₃ | 4-Cl | CH₂=C—CH₂<br>\|<br>CH₃ | 135–139°/0,001 Torr |
| 70 | Cl | 6-CH₃ | C₂H₅ | 153°/0,01 Torr |
| 71 | Cl | 6-CH₃ | C₃H₇ | 141°/0,01 Torr |
| 72 | Cl | 6-CH₃ | C₄H₉ | 140°/0,001 Torr |
| 73 | Cl | 6-CH₃ | (CH₃)₂—CH | 155°/0,01 Torr |
| 74 | Cl | 6-CH₃ | (CH₃)₃C | |
| 75 | Cl | 6-CH₃ | CH₂=CH—CH₂ | 146°/0,01 Torr |
| 76 | Cl | 6-CH₃ | (CH₃)₂CH—CH₂ | 140°/0,005 Torr |
| 77 | Cl | 6-CH₃ | CH₂=CCl—CH₂ | |
| 78 | Cl | 6-CH₃ | ClCH—CH—CH₂ | |
| 79 | Cl | 6-CH₃ | ClCH—CCl—CH₂ | |
| 80 | Cl | 6-CH₃ | CH₃—CH=CH—CH₂ | |
| 81 | Cl | 6-CH₃ | CH₂=C—CH₂<br>\|<br>CH₃ | 130–135°/0,001 Toor |
| 82 | C₂H₅ | 6-C₂H₅ | C₂H₅ | 119–123°/0,001 Torr |
| 83 | C₂H₅ | 6-C₂H₅ | C₃H₇ | |
| 84 | C₂H₅ | 6-C₂H₅ | C₄H₅ | |
| 85 | C₂H₅ | 6-C₂H₅ | (CH₃)₂CH | |
| 86 | C₂H₅ | 6-C₂H₅ | (CH₃)₃C | |
| 87 | C₂H₅ | 6-C₂H₅ | CH₂=CH—CH₂ | 112–118°/0,001 Torr |
| 88 | C₂H₅ | 6-C₂H₅ | (CH₃)₂CH—CH₂ | 129–132°/0,001 Torr |
| 89 | C₂H₅ | 6-C₂H₅ | CH₂=CCl—CH₂ | |
| 90 | C₂H₅ | 6-C₂H₅ | ClCH=CH—CH₂ | |
| 91 | C₂H₅ | 6-C₂H₅ | ClCH—CCl—CH₂ | |
| 92 | C₂H₅ | 6-C₂H₅ | CH₃—CH=CH—CH₂ | |
| 93 | C₂H₅ | 6-C₂H₅ | CH₂=C—CH₂<br>\|<br>CH₃ | |
| 94 | CH₃ | 6-CH₃ | C₂H₅ | 135–140°/0,001 Torr |
| 95 | CH₃ | 6-CH₃ | C₃H₇ | 140°/0,001 Torr |
| 96 | CH₃ | 6-CH₃ | (CH₃)₂CH | 145°/0,001 Torr |
| 97 | CH₃ | 6-CH₃ | C₄H₉ | 148°/0,001 Torr |
| 98 | CH₃ | 6-CH₃ | (CH₃)₂CH—CH₂ | 128°/0,001 Torr |
| 99 | CH₃ | 6-CH₃ | (CH₃)₃—C | 135°/0,001 Torr |
| 100 | CH₃ | 6-CH₃ | CH₂=CH—CH₂ | 146°/0,001 Torr |
| 101 | CH₃ | 6-CH₃ | CH₂=C—CH₃<br>\|<br>CH₃ | 122–127°/0,001 Torr |

The thiazolines of the formula I possess excellent properties for combatting acarids, especially ticks (Ixodidae), such as Amblyomma, Rhipicephalus and Boophilus. This applies in particular to the oviposition of fertile eggs. Furthermore, these compounds have an intensive detaching effect, which is of special importance for the treatment of host animals already infested (e.g. cattle or rabbits). The detaching effect commences immediately after application of the active substance, as a consequence of which the ticks are prevented from continuing the absorption of their food, namely, the extraction of blood. They detach themselves in the course of treatment from the host animal, the end effect of which is the complete removal of the pests from the treated animal.

EXAMPLE 3

Test to determine the effect on ticks: inhibition of oviposition

The test insects used are females of the cattle tick *Boophilus microplus* which have sucked themselves full. There are treated per concentration 10 ticks of a resistant strain and 10 ticks of a normally sensitive strain. The ticks are immersed for a short time in aqueous emulsions or aqueous solutions of the salts of the compounds to be examined. They are fixed on plates covered with double adhesive tape and kept in an air-conditioned chamber under constant conditions. An evaluation is made after three weeks, and the overall inhibition of the oviposition of fertile eggs is determined.

The inhibitory effect of the substances is expressed in terms of substance concentration in ppm to produce a 100% effect against normally sensitive adult female ticks and resistant adult female ticks, respectively.

Results:

| Compound | minimum concentration in ppm for 100% inhibitory effect | |
|---|---|---|
| | δ sensitive | δ resistant |
| 1) 2-(2,6-dichlorophenylimino)-3-methyl-thiazoline | 10 | 10 |
| 2) 2-(2-chloro-6-methylphenylimino)-3-methyl-thiazoline | ≦50 | ≦50 |
| 3) 2-(2,6-diethylphenylimino)-3-methyl-thiazoline | ≦50 | ≦50 |
| 4) 2-(2-methyl-4-chlorophenylimino)-3-methyl-thiazoline | 10 | 5 |
| 5) 2-(2,4-dimethylphenylimino)-3-methyl-thiazoline | 10 | 10 |
| 6) 2-(2-methyl-6-ethylphenylimino)-3-methyl-thiazoline | ≦50 | ≦50 |

Toxicity test: $DL_{50}$ rat p.o.
Compound No. 4: 2500 mg/kg

Comparative results with known compounds

| Compound | Minimum concentration in ppm for 100% inhibitory effect | |
|---|---|---|
| | δ sensitive | δ resistant |
| 2-(3,4-dichlorophenylimino)-N-n-butyl-pyrrolidine (Bimarit) | 1000 | 1000 |
| 2-(3,4-dichlorophenylimino)-3-methyl-thiazoline (Swiss Patent Specification No. 439,858) | >1000 | >1000 |
| 2-(3,4-dichlorophenylimino)-3-methyl-thiazoline-HCl (Swiss Patent Specification No. 439,858) | >1000 | >1000 |
| 2-(4-chlorophenylimino)-3-methyl-thiazoline-HCl (Swiss Patent Specification No. 439,858) | >1000 | >1000 |

EXAMPLE 4

Test for action against ticks: detaching-effect

Adult ticks and nymphs are placed onto rabbits' ears, with the ears then being covered sack-like with textile fabric to prevent the pests from escaping. Before the treatment, the covering is removed and the infestation recorded. The infested ears are immersed for about 2 minutes in a 0.05% solution of the substance to be tested. The test solution used is an aqueous dilution of an emulsion concentrate of the respective substance. The covering is then again fixed in position. An evaluation is made after 24 hours. The effectiveness of the tested substance is expressed as the percentage of ticks detached relative to the number of ticks attached to the rabbit's ears before the treatment.

Results:

| Compound | Detaching-effect in % of detached ticks | | |
|---|---|---|---|
| | Amblyomma hebraeum | | Rhipicephalus bursa |
| | adults ♀,♂ | nymphs | |
| 2-(2-methyl-4-chlorophenyl-imino)-3-methyl-thiazoline | 100 | 100 | 100 |
| 2-(2,4-dimethylphenylimino)-3-methyl-thiazoline | 100 | 100 | 100 |

Comparative test with a known compound

A cow is infested with Amblyomma-females and, after the ticks have sucked themselves firmly onto the animal within 1 - 2 days, it is sprayed with an emulsion-concentrate solution diluted with water, with the concentration of active substance being 0.05%.

Results:

| Compound | Detaching-effect number of attached ticks | |
|---|---|---|
| | before treatment | after treatment |
| 2-(2-methyl-4-chlorophenyl-imino)-3-methyl-thiazoline | 60 | 0 |
| 2-(2,4-dimethylphenylimino)-3-methyl-thiazoline | 60 | 0 |
| BIMARIT | 75 | 73 |

The compounds of the formula I can be used on their own or together with suitable carriers and/or additives. Suitable carriers and additives may be solid or liquid, and correspond to the substances common in formulation practice, such as natural or regenerated substances, solvents, dispersing agents, wetting agents, adhesives, thickeners, binders and/or fertilisers.

For application, the compounds of the formula I can be processed into the form of dusts, emulsion concentrates, granulates, dispersions, sprays or solutions, the formulation of these preparations being effected in a manner commonly known in the art. Also to be mentioned are cattle dips and spray races, as well as the pour-on method, in which aqueous preparations or concentrates are used.

The compositions according to the invention are produced in a manner known per se by the imtimate mixing and/or grinding of active substances of the formula I with suitable carriers, optionally with the addition of dispersing agents or solvents which are inert to the active substances. The active substances can be obtained and used in the following forms:

Solid preparations: dusts, scattering agents or granulates;

Liquid preparations:
 a. water-dispersible concentrates of active substance: wettable powders, pastes or emulsions;
 b. solutions.

The content of active substance in the preparations described in the foregoing is between 1 and 80%.

EXAMPLE 4

Emulsion concentrate 20 parts by weight of the aforementioned active substance are dissolved in 70 parts by weight of xylene, and there are then added 10 parts by weight of an emulsifier consisting of a mixture of an arylphenyl-polyglycol ether and the calcium salt of dodecylbenzenesulphonic acid. Water may be added to the emulsion concentrate in any desired proportion to form a milky emulsion.

EXAMPLE 5

Emulsion concentrate 5 to at most 30 parts by weight of active substance are dissolved with stirring at room temperature in 30 parts by weight of dibutylphthalate, 10 parts by weight of Solvent 200 (low-viscous, highly aromatic petroleum distillate), and 15 to 35 parts by weight of Dutrex 238 FC (viscous, highly aromatic petroleum distillate), and there are then added 10 parts by weight of an emulsifier mixture consisting of castor oil-polyglycol ether and the calcium salt of dodecylbenzenesulphonic acid. The emulsion concentrate obtained in this manner gives milky emulsions when water is added.

EXAMPLE 6

Wettable powder 5 to 30 parts by weight of the active substance are thoroughly mixed, in a mixing apparatus, with 5 parts by weight of an absorbing carrier material (Kieselsaeure K 320 or Wessalon S) and 55 to 80 parts by weight of a carrier material (bolus alba or Kaolin B 24) and a dispersing agent mixture consisting of 5 parts by weight of a Na-lauryl sulphonate and 5 parts by weight of an alkyl-aryl-polyglycol ether. This mixture is ground in a dowelled disc mill or air-jet mill to 5 – 15 μm. The wettable powder obtained in this manner gives a good suspension in water.

EXAMPLE 7

Dust 5 parts by weight of finely ground active substance are thoroughly mixed with 2 parts by weight of a precipitated silicic acid and 93 parts by weight of talcum.

We claim:

1. A thiazoline compound of the formula

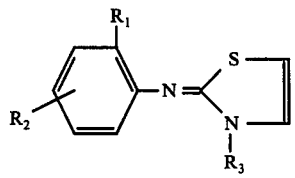

(I)

wherein $R_1$ and $R_2$, independently of one another, represent chlorine, methyl or ethyl, whereby $R_2$ can occupy the 4- or 6-position, with the exception that if $R_1$ and $R_2$ represent chlorine, $R_2$ cannot be in the 4-position, $R_3$ represents a straight-chain or branched-chain alkyl having 1 to 4 carbon atoms, a straight-chain or branched-chain alkyl of 1 to 4 carbon atoms, substituted by alkoxy having 1–2 carbon atoms, a straight-chain or branched-chain alkenyl having 3 to 5 carbon atoms, or a straight-chain or branched-chain alkenyl of 3 to 5 carbon atoms substituted by halogen, and the acid addition salts thereof selected from the group consisting of hydrochlorides, sulfates, phosphates, perchlorates, acetates, lactates, succinates, citrates and naphthalenedisulfonates.

2. Compound according to claim 1 of the formula

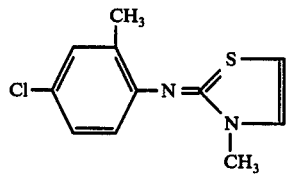

3. Compound according to claim 1 of the formula

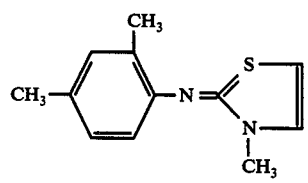

4. An acaricidal composition comprising an acaricidally effective amount of a compound according to claim 1, together with a suitable carrier therefor.

5. The composition of claim 4, wherein said acarid is ticks.

6. A method for combatting acarids comprising applying to the locus thereof an acaricidally effective amount of a compound according to claim 1.

7. The method of claim 6, wherein said compound corresponds to the formula

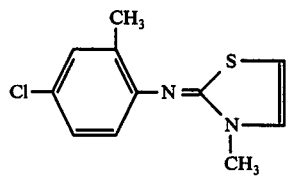

8. The method of claim 6, wherein said compound corresponds to the formula

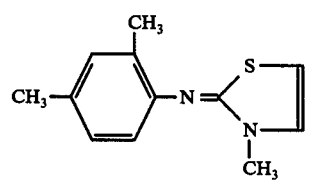

9. The method of claim 6, wherein said acarid is ticks.

* * * * *

UNITED STATES PATENT AND TRADEMARK OFFICE
CERTIFICATE OF CORRECTION

PATENT NO. : 4,079,144
DATED : March 14, 1978
INVENTOR(S) : Dieter Dürr, Walter Traber It is certified that error appears in the above-identified patent and that said Letters Patent is hereby corrected as shown below:

Column 10, Claim 2, Line 2, should read --

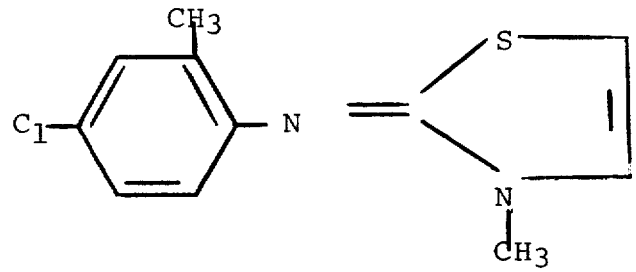

Column 10, Claim 3, Line 2, should read --

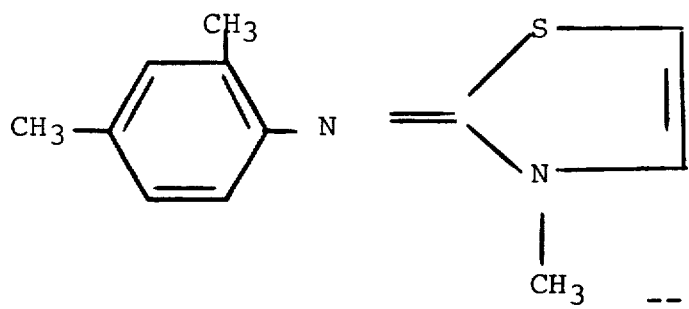

--.

Signed and Sealed this

Twelfth Day of August 1986

[SEAL]

Attest:

DONALD J. QUIGG

Attesting Officer  Commissioner of Patents and Trademarks